(12) United States Patent
Walker et al.

(10) Patent No.: US 9,248,381 B2
(45) Date of Patent: Feb. 2, 2016

(54) METHOD OF PURIFYING A DICARBOXYLIC ACID

(75) Inventors: Thomas Chad Walker, Independence, KY (US); Stephen W. Turner, Hamilton, OH (US); Jay William Landwehr, Villa Hills, KY (US); Douglas da Silva Rosa, Cincinnati, OH (US); Mark Elliot Durchholz, West Chester, OH (US)

(73) Assignee: Emery Oleochemicals LLC, Cincinnati, OH (US)

( * ) Notice: Subject to any disclaimer, the term of this patent is extended or adjusted under 35 U.S.C. 154(b) by 985 days.

(21) Appl. No.: 13/358,943

(22) Filed: Jan. 26, 2012

(65) Prior Publication Data

US 2012/0197043 A1     Aug. 2, 2012

Related U.S. Application Data

(60) Provisional application No. 61/437,589, filed on Jan. 29, 2011.

(51) Int. Cl.

| | |
|---|---|
| *C07C 51/43* | (2006.01) |
| *C07C 51/44* | (2006.01) |
| *C07C 51/34* | (2006.01) |
| *B01D 3/12* | (2006.01) |
| *B01D 1/22* | (2006.01) |
| *B01D 3/04* | (2006.01) |

(52) U.S. Cl.
CPC .. *B01D 3/12* (2013.01); *B01D 1/22* (2013.01); *B01D 3/04* (2013.01); *C07C 51/34* (2013.01); *C07C 51/43* (2013.01); *C07C 51/44* (2013.01)

(58) Field of Classification Search
CPC .......... C07C 51/43; C07C 41/44; C07C 51/34
USPC ....................................................... 562/523
See application file for complete search history.

(56) References Cited

U.S. PATENT DOCUMENTS

| | | |
|---|---|---|
| 1,554,483 A | 9/1925 | Bailey et al. |
| 2,389,191 A | 11/1945 | Fitzpatrick et al. |
| 2,450,858 A | 10/1948 | Fitzpatrick et al. |
| 2,813,113 A | 11/1957 | Goebel et al. |
| 2,916,502 A | 12/1959 | Allen et al. |
| 3,402,108 A | 9/1968 | Oehlschlaeger et al. |
| 3,522,093 A | 7/1970 | Woolman |
| 4,013,579 A | 3/1977 | Nakasone et al. |
| 4,185,025 A | 1/1980 | Carduck et al. |
| 4,242,309 A | 12/1980 | Carduck et al. |
| 5,399,749 A | 3/1995 | Rebrovic |
| 5,420,316 A | 5/1995 | Rebrovic |
| 5,543,565 A | 8/1996 | McVay et al. |
| 5,801,275 A | 9/1998 | McVay et al. |
| 5,883,269 A | 3/1999 | Rebrovic |
| 5,973,173 A | 10/1999 | Josten et al. |
| 6,362,368 B1 | 3/2002 | Frische et al. |
| 6,455,715 B1 | 9/2002 | Frische et al. |
| 2002/0068837 A1 | 6/2002 | Frische et al. |
| 2007/0276165 A1 | 11/2007 | Gutsche et al. |

FOREIGN PATENT DOCUMENTS

| | | |
|---|---|---|
| CN | 101250101 A | 9/2010 |
| EP | 0536747 A2 | 4/1993 |
| EP | 1074540 A1 | 5/2003 |
| WO | 9836045 A1 | 8/1998 |
| WO | 0068346 A1 | 11/2000 |
| WO | 2009133465 A2 | 11/2009 |

OTHER PUBLICATIONS

European Patent Office, International Search Report and Written Opinion for PCT/US2012/022709, 12pp.
European Patent Office, International Search Report and Written Opinion for PCT/US2012/022718, 12pp.
Machine-generated English translation of Abstract from CN101250101.
Espacenet, EPO English Abstract of Application No. WO 2009/133465 (A2), Published Nov. 5, 2009, http://worldwide.espacenet.com, retrieved Feb. 13, 2013, 1 pg.
European Patent Office, International Search Report and Written Opinion in corresponding PCT Application No. PCT/US2012/022722, mailed Dec. 11, 2012, 17 pp.
European Patent Office, International Search Report and Written Opinion in corresponding PCT Application No. PCT/US2012/022718, mailed Aug. 8, 2013, 9 pp.
Written Opinion issued by the Intellectual Property Office of Singapore in related Patent Application No. 2013079892, mailed on Jul. 23, 2014 (9 pages).

*Primary Examiner* — Shawquia Jackson

(74) *Attorney, Agent, or Firm* — Wood, Herron & Evans, LLP

(57) ABSTRACT

A process for purifying a dicarboxylic acid that is derived from the mixed oxidation products from an ozonization of a mixture containing an ethylenically unsaturated compound having between 6 to 24 carbons, the process includes distilling the mixed oxidation products to provide a first distillate, and a second distillate, where the second distillate includes the dicarboxylic acid and impurity acids, partitioning the second distillate between water and a organic solvent, separating the organic solvent layer from the water layer, lowering the temperature of the water layer to crystallize at least a portion of the dicarboxylic acid, separating the crystallized dicarboxylic acid solid, melting the crystallized dicarboxylic acid, and distilling the liquid dicarboxylic acid to provide a purified dicarboxylic acid.

18 Claims, 4 Drawing Sheets

METHOD OF PURIFYING A DICARBOXYLIC ACID

FIELD OF THE INVENTION

The present invention relates to a method of purifying a dicarboxylic acid compound, which was obtained from the oxidative ozonolysis of unsaturated compounds and to apparatus for carrying out the method.

BACKGROUND OF THE INVENTION

Commercial production of azelaic acid and pelargonic acid has been realized via an oxidative cleavage of an alkenyl (—C=C—) unit in oleic acid. For example, azelaic acid has been prepared from oleic acid by oxidation with chromium sulfate, as disclosed in U.S. Pat. No. 2,450,858. However, because stoichiometric use of chromium reagents is undesirable, a more efficient approach utilizing ozone has been developed, as disclosed and described in U.S. Pat. Nos. 2,813,113; 5,801,275; 5,883,269; and 5,973,173.

The basic process will be best understood by referring to the description in the accompanying FIG. 1, which is a diagrammatic flow chart indicating the pieces of equipment used and their relationship in the ozonolysis process. Referring to FIG. 1, oleic acid is supplied to a feed tank 10 and then to an ozone absorber 13, wherein the oleic acid is flowed countercurrent to a continuous flow of a gaseous mixture comprising oxygen/ozone gas introduced to the ozone absorber 13. The ozone absorber 13 is cooled or refrigerated to substantially control the temperature of the reaction occurring therein.

The ozone absorber 13 receives ozonized oxygen gas by a continuous closed system through which the oxygen circulates. Thus, a given quantity of oxygen is used and reused multiple times and the system need be bled and fed with makeup oxygen only to a small extent to maintain the oxygen content at a predetermined high level by replacing oxygen consumed after a portion has been converted to ozone. The circulating oxygen system comprises an oxygen supply 16 that leads to a dehydrator 19. From the dehydrator 19, the oxygen is transferred to an ozone generator 22, which converts a quantity of the oxygen to ozone by using electricity. From the ozone generator 22, a gaseous mixture containing ozone and oxygen passes into the ozone absorber 13 in which substantially all of its ozone content is absorbed by the oleic acid as further explained below. During the residence time of the oleic acid ozonide-containing mixture in the ozone absorber 13, the mixture may increase in viscosity. If desired, the viscosity of the mixture may be reduced by introducing compatible diluents, such as pelargonic acid, as discussed further below.

Upon exiting the ozone absorber 13, the gas mixture, now substantially devoid of ozone, passes to an electrostatic precipitator 25, which removes any fine mist organic matter that may have been picked up in the ozone absorber 13. The purified gas mixture then passes from the electrostatic precipitator 25 through a compression pump 28 to a cooler 31 and then returns to the dehydrator 19, in which substantially all moisture is removed from the gas mixture. Between the cooler 31 and the dehydrator 19, oxygen-containing gas, which may be controlled by an ozone generating system valve 34, may be supplied to the ozonide decomposing system reactor 37.

The aforementioned absorption of ozone by oleic acid forms oleic acid ozonides, which are transferred to the ozonide decomposing system reactor 37 and treated with oxygen bled from the ozone generating system valve 34. The ozonide decomposing system reactor 37 may be any type device which is adapted to provide substantial interfacial contact between a liquid and a gas and which may be cooled to moderate the temperature of the reaction. The oxygen bled from the ozone generating system is fed into the bottom of the ozonide decomposing system reactor 37 and is agitated with the liquid in each tank by means of mechanical agitators which are not shown.

While only one integral ozonide decomposing system reactor 37 is shown in the drawing, it is to be understood that the reactor 37 may comprise distinct regions configured for independent temperature control, independent pressure control, or both. Alternatively, any number of reactors may be used depending upon the size of the reactors, the rate of the flow of the ozonides and their decomposition products, and the efficiency of the agitation in effecting contact between the oxygen gas and the liquid being treated. Further, alternative embodiments having more than one reactor may be connected in a series configuration, a parallel configuration, or both.

Temperature control is an important operating parameter for the ozonide decomposing system reactor 37. More specifically, the incoming stream of ozonides must be heated to reach a suitable reaction temperature at which the ozonide moiety may efficiently undergo oxidative decomposition upon exposure to one or more catalysts to preferentially form an aldehyde and a carboxylic acid. The ozonide decomposition catalysts may include Brønsted-Lowry acids, Brønsted-Lowry bases, Lewis acids, Lewis bases, metals, or salts and soaps thereof. Exemplary ozonide decomposition catalysts may include at least in part, Na, K, B, Sn, Zn, Pt, Pd, Rh, Ag, Mn, Cu, Ni, titania/silica or titania/$P_2O_5$ composites, and combinations thereof. The catalyst can be introduced into the process in the form of a soluble material or in the form of a solid or supported catalyst.

After reaching a suitable reaction temperature, further oxidation of the aldehyde functional group to an acid functional group may occur at a rate sufficient to generate heat, which may in turn contribute to elevating the temperature of the incoming stream of ozonides. However, cooling water may need to be supplied in order to prevent the temperature from rising above a predetermined level. As such, the temperature is controlled in order to be suitable for efficient oxidation to convert the ozonides to mixed oxidation products. In FIG. 1, the heating and cooling apparatus are not shown.

From the ozonide decomposing system reactor 37, the mixed oxidation products pass to a first distillation unit 40 wherein pelargonic acid and other carboxylic acids are distilled from the mixed oxidation products to form a first distillate and a first residue of the mixed oxidation products. The first distillate, which contains pelargonic acid, is converted to a liquid in a first condenser 43 and then is delivered to a crude pelargonic acid storage tank 46. However, some of the crude pelargonic acid may be used to dilute the oleic acid reactant and the oleic acid ozonides in the absorber 13 if desired. Thus, pelargonic acid, which may be crude or further purified, may be added to the ozone absorber 13 in order to reduce the viscosity of the ozonides in the absorber 13. The amount of recycled pelargonic acid supplied to the absorber 13 may be controlled with a valve 49.

It should be noted that other viscosity reducers and diluents may be used. The diluents can be known materials which do not readily react with ozone and which are compatible with the ozonides or the reaction products, or can be a portion of the reaction product. Such diluents include, but are not limited to, saturated short chain acids such as acetic acid, butanoic acid, caproic acid, heptanoic acid, caprylic acid, pelargonic acid, and capric acid; esters such as ethyl acetate and butyl acetate; and alkanes such as hexane, octane, and decane. However, the use of pelargonic acid is recommended because, as an end product of the process, it does not interfere with the operation of the circulating oxygen system and requires no separate distillation. In other words, since pelargonic acid is one of the end products of the process, it is an ideal diluent.

The first residue of the mixed oxidation products, now stripped of a substantial portion of the available pelargonic acid, is next conveyed to an azelaic acid distillation unit 52 in which a portion of the first residue of the mixed oxidation products is distilled to form a second distillate, which includes azelaic acid, and a second residue of the mixed oxidation products. The second distillate is condensed by passage through an azelaic acid distillate condenser 55 to form a crude azelaic acid, which is transferred to a crude azelaic acid storage tank 58. The second residue of the mixed oxidation products or pitch that remains after distilling away the second distillate is removed from the azelaic acid distillation unit 52 and transferred to residue storage 61. The second residue of the mixed oxidation products may still contain some amount of azelaic acid, so further processing, if desired, can occur to recover a portion thereof.

The crude azelaic acid condensate may also contain a wide variety of by-product acids (BPA), such as monocarboxylic acids of undetermined identity with the majority being C6 to C18 monocarboxylic acids. These monocarboxylic acids usually comprise 15 to 20% of the crude azelaic acid condensate. The next step in the process is to purify the crude azelaic acid.

From the crude azelaic acid storage tank 58, the crude azelaic acid is transferred to extractor 64 where the crude azelaic acid is extracted with hot water (e.g., about 175° F., about 80° C. to about 210° F., about 99° C.) to form a hot aqueous solution of azelaic acid. The by-product acids (BPA) that do not dissolve in the hot aqueous azelaic acid solution are decanted from the extractor 64 to BPA storage 67. Meanwhile, the hot aqueous azelaic acid solution is transferred to an evaporator 70 in which water is removed therefrom. Next, azelaic acid in molten form is fed from the evaporator 70 to a flaker 73 where the temperature is reduced to below the melting point, and then solid flakes of azelaic acid are conveyed to an azelaic acid storage bin 76.

While the process and apparatus described above provide azelaic and pelargonic acids from oleic acid, deficiencies exist with respect to the final purity and yield of the azelaic acid. For example, the method described above yields a final azelaic acid with an undesirable level of monocarboxylic acid impurities, which will interfere with the linear propagation for certain polymerization processes by terminating the chain growth. While various crystallization and/or distillation techniques have been utilized to attain the desired levels of monocarboxylic acid impurities, they result in lower product yield and/or lower quality product due to undesirable coloring, respectively. As such, new and/or improved processes and apparatus are needed.

SUMMARY OF THE INVENTION

According to embodiments of the present invention, a process for purifying a dicarboxylic acid is provided. The process includes ozonizing a mixture comprising an ethylenically unsaturated compound having between 6 to 24 carbons with an ozone-containing gas to form a plurality of ozonization products; and cleaving the plurality of ozonization products under oxidative conditions in the presence of a suitable catalyst to form mixed oxidation products, wherein the mixed oxidation products comprises a mixture of C2 to C22 monocarboxylic acids and C2 to C22 dicarboxylic acids that includes the dicarboxylic acid. The process further includes distilling the mixed oxidation products to provide a first distillate comprising a portion of the C2 to C22 monocarboxylic acids, and a first residue of the mixed oxidation products, wherein the first residue of the mixed oxidation products comprises the dicarboxylic acid and a plurality of impurity acids; distilling the first residue of the mixed oxidation products to provide a second distillate and a second residue of the mixed oxidation products, wherein the second distillate comprises the dicarboxylic acid and a first fraction of the plurality of impurity acids; and partitioning the second distillate between water and an organic solvent, wherein the water is at a temperature within the range of about 175° F., 79° C. to about 230° F., 110° C. Water and the organic solvent are substantially immiscible to thereby form an aqueous layer containing the dicarboxylic acid and an organic solvent layer containing a second fraction of the plurality of impurity acids. The process further includes separating the organic solvent layer from the aqueous layer; lowering the temperature of the aqueous layer to crystallize at least a portion of the dicarboxylic acid from the aqueous water layer to provide a crystallized dicarboxylic acid solid and a mother liquor containing uncrystallized dicarboxylic acid and a major portion of a third fraction of the plurality of impurity acids; separating the crystallized dicarboxylic acid solid from the mother liquor to provide a first batch of the dicarboxylic acid comprising the crystallized dicarboxylic acid solid; melting the first batch of the dicarboxylic acid to form a liquid comprising the dicarboxylic acid; and distilling the liquid comprising the dicarboxylic acid to provide a purified dicarboxylic acid.

In accordance with another embodiment of the invention, at least one chemical derivative of a dicarboxylic acid afforded by the processes claimed herein is provided.

DETAILED DESCRIPTION OF THE INVENTION

Figure 1:
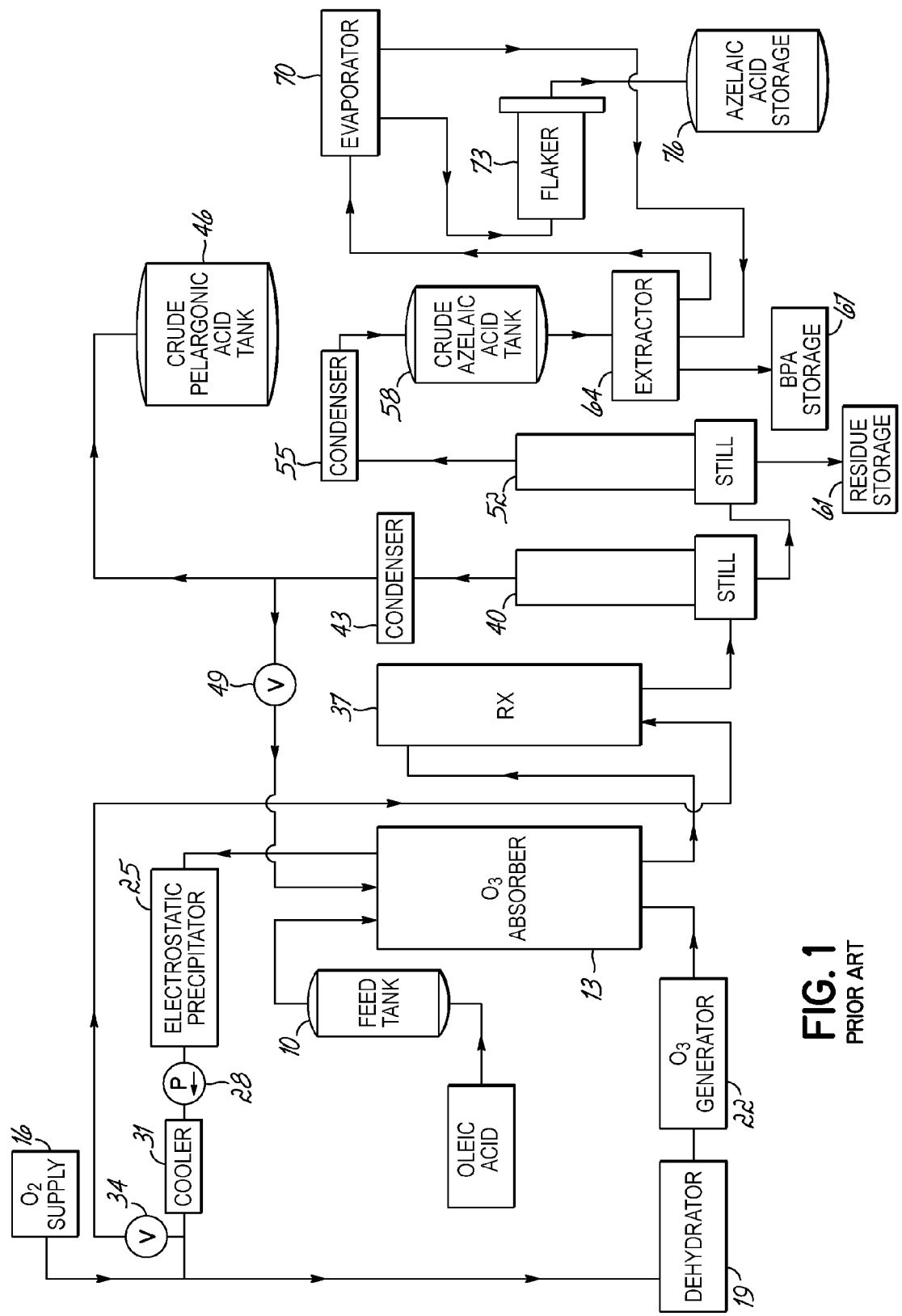
FIG. 1 is a schematic representation of an oleic acid ozonolysis plant (under the prior art).

According to embodiments of the present invention, a method of purifying a dicarboxylic acid compound is provided. The dicarboxylic acid is derived from a chemical process where an ethylenically unsaturated compound is contacted with ozone to obtain a plurality of ozonide products. The ozonide products are treated with an oxygen gas and at least one catalyst in a reactor to obtain mixed oxidation products comprising a monocarboxylic acid and a dicarboxylic acid. The mixed oxidation products are subjected to a multi-step purification process wherein at least a portion of the monocarboxylic acid is separated therefrom in a first distillation fraction thereby leaving the dicarboxylic acid in a first residue of the mixed oxidation products. The purification of the dicarboxylic acid contained within the first residue of the mixed oxidation products is effected by combining an extraction process using an organic solvent, a multi-stage recrystallization, and a final distillation.

According to one embodiment, the ozonolysis may be performed on ethylenically unsaturated compounds. Suitable ethylenically unsaturated compounds are not particularly limited by their source and may include any number of carbon atoms, such as between 6 to 24 carbon atoms. The ethylenically unsaturated compounds may include between 12 to 20 carbon atoms. For example, the ethylenically unsaturated compounds may have 18 carbon atoms. Further, the ethylenically unsaturated compounds may include additional functional groups, such as carboxylic acids. The ethylenically unsaturated compounds may be derived from animal or plant sources. Accordingly, the ethylenically unsaturated compounds include fatty acids, including those obtained from palm oil or tallow. In one example, the ethylenically unsaturated compounds include oleic acid.

After reacting a C6 to C24 ethylenically unsaturated compound with an ozone-containing gas, a plurality of ozonization products are formed, which are cleaved under oxidative conditions in the presence of a suitable catalyst to form mixed oxidation products, which comprise a mixture of C2 to C22 monocarboxylic acids and C2 to C22 dicarboxylic acids. For example, the mixture of carboxylic acids may include C2 to C16, C5 to C9, or C6 to C18 monocarboxylic acids. The mixture of carboxylic acids may include C2 to C16, C5 to C9, or C6 to C18 dicarboxylic acids, for example. According to an exemplary embodiment, the ozonolysis may be performed on oleic acid to thereby produce pelargonic acid, which is a saturated C9 monocarboxylic acid, and azelaic acid, which is a saturated C9 dicarboxylic acid.

In order to isolate a desired dicarboxylic acid, such as azelaic acid, the mixed oxidation products, which may be oleic acid derived, are distilled under a first set of distillation conditions to provide a first distillate comprising a portion of the C2 to C22 monocarboxylic acids, which can include pelargonic acid, and a first residue of the mixed oxidation products. The first residue of the oxidation products comprises the desired dicarboxylic acid (e.g., azelaic acid), along with a plurality of impurity acids, which may include undesired long chain (e.g., C9 to C22) monocarboxylic acids and other dicarboxylic acids.

The first residue is then subjected to a second distillation performed under a second set of distillation conditions to provide a second distillate and a second residue of the mixed oxidation products. The second distillate comprises the desired dicarboxylic acid, such as azelaic acid, and a first fraction of the plurality of impurity acids.

In order to separate the azelaic acid from the bulk of the plurality of impurity acids (i.e., by-product acids), further processing includes an aqueous extraction, a crystallization, and a distillation, as explained next. The aqueous extraction includes partitioning the second distillate in water and/or between water and an organic solvent that is substantially immiscible with water. Accordingly, the second distillate is combined with hot water to form a concentrated aqueous solution of the second distillate. If desired, a portion of the by-product acids (BPA) that do not dissolve in the hot aqueous azelaic acid solution can be decanted from the concentrated aqueous solution in a separate extractor prior to subsequently extracting the concentrated aqueous solution cut with an organic solvent. In either case, the concentrated aqueous solution of second distillate is then mixed with the organic solvent, where the azelaic acid is retained in the water layer, i.e., the aqueous phase, along with a second fraction of the plurality of impurity acids, such as various water-soluble short chain (e.g., C4 to C8) dicarboxylic acids. The organic solvent soluble by-product acids are extracted into the organic solvent.

Figure 2:
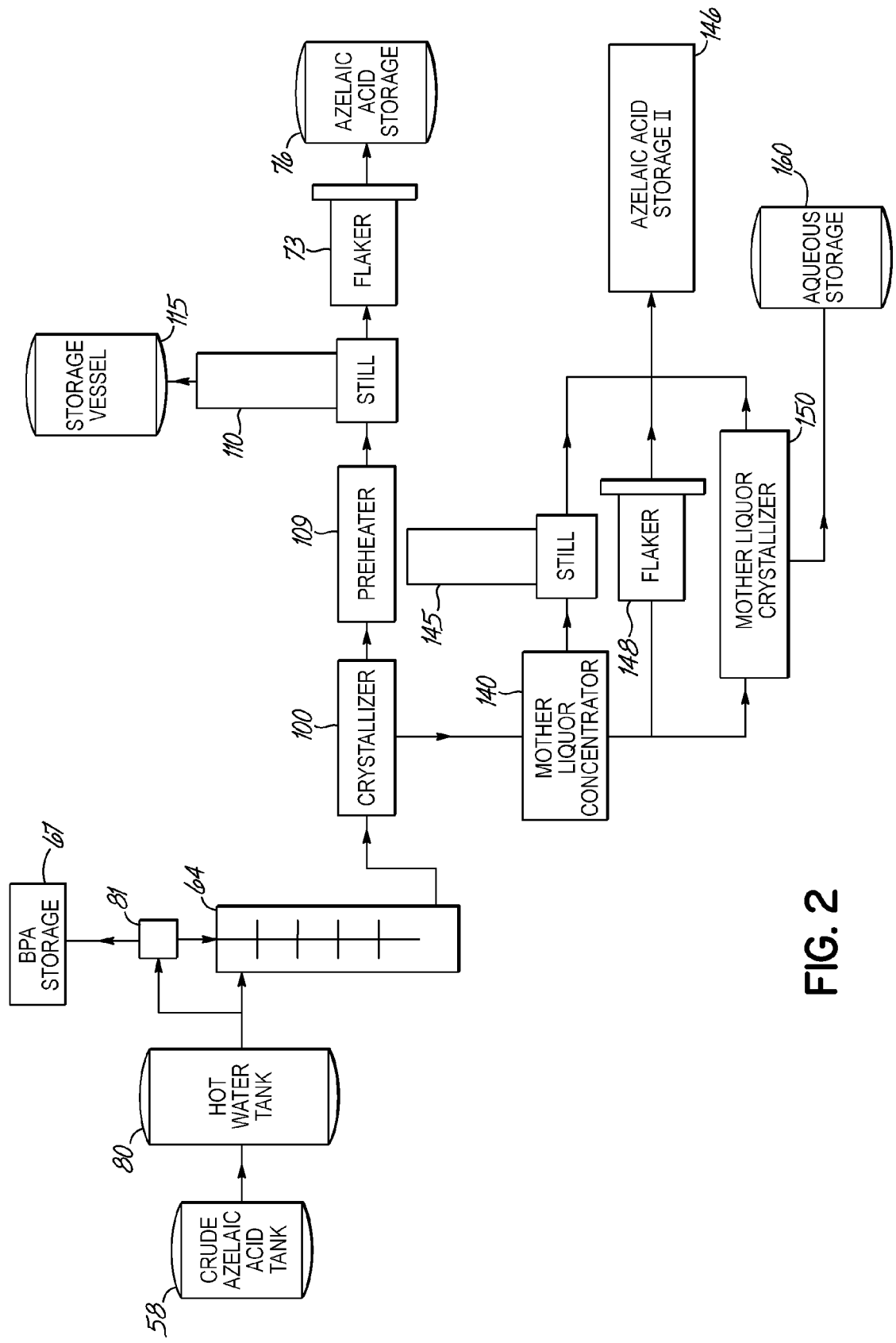
FIG. 2 is a schematic representation of an azelaic acid purification procedure according to an embodiment of the invention.

With reference to FIG. 2, the crude azelaic acid (i.e., the second distillate) from storage tank 58 may be combined with water in a hot water tank 80 to make a concentrated aqueous solution of crude azelaic acid, which may then be fed into decanter 81, where a portion of the by-product acids (BPA) that do not dissolve in the hot aqueous azelaic acid solution can be decanted from the concentrated aqueous solution, prior to transfer to the extractor 64, where the concentrated aqueous solution cut is then mixed with the organic solvent. According to one embodiment, the concentrated aqueous solution of crude azelaic acid may be directly fed into extractor 64. According to one embodiment, the aqueous stream and the organic solvent are intermixed in a counter-flow manner. According to one embodiment, the azelaic extractor 64 may be a York-Scheibel extractor, which is a counter-current, multistage, continuous liquid-liquid extractor. In one embodiment, the York-Scheibel extractor has about 10 to about 60 stages. For example, the York-Scheibel extractor may have 10, 20, 30, 40, 50, or 60 or more stages.

Azelaic acid is soluble in hot water. The extraction temperature of the water may be within the range of about 175° F., 79° C. to about 230° F., 110° C. The organic solvent is not particularly limited to any specific solvent, but should be substantially immiscible with water. For example, the organic solvent may have water solubility of less than 0.5 grams per liter at 20° C. Further, suitable organic solvents have boiling points greater than the temperature of the extracting water under the extraction pressure.

Exemplary organic solvents that can be used in the process include, but are not limited to, an aliphatic or aromatic hydrocarbon solvent and/or mixtures thereof in which the impurities present in the crude dicarboxylic acid are soluble and in which the dicarboxylic acid is substantially insoluble. Examples of such aliphatic solvents include, but are not limited to, linear and branched, cyclic and acyclic alkanes such as pentane, hexane, heptane, octane, 2,2,4-trimethylpentane, cyclopentane, cyclohexane, methylcyclopentane, methylcyclohexane; alkenes such as pentene, hexene, heptene, cyclopentene, cyclohexene, methylcyclopentene, methylcyclohexene and the like; and liquefied hydrocarbons that are normally gases at room temperature and pressure such as liquid propane and liquid butane. Examples of such aromatic solvents include, but are not limited to, benzene, toluene, and xylene. Solvent mixtures include, but are not limited to, petroleum distillates such as naphtha, heavy naphtha and petroleum ether. In one example, the organic solvent is octane. In another example, the organic solvent is a heavy naphtha, such as VM&P Naphtha.

According to an embodiment, crude azelaic acid from storage tank 58 is mixed with water in a hot water tank 80, where the water is at a temperature within the range of about 175° F., 79° C. to about 230° F., 110° C., to make the concentrated aqueous solution of crude azelaic acid, which is then fed into the decanter 81 and then transferred to the extractor 64 and mixed with the organic solvent. On discharge from the extractor 64, the organic solvent content of the extracted aqueous solution of azelaic acid should be as low as possible to avoid introducing flammable organic solvents into other parts of the plant while transferring the extracted aqueous solution to a crystallizer 100. A flash tank may be used to remove the organic solvent.

The organic phase comprising the organic solvent and extracted by-product acids (BPA), such as C9 to C22 monocarboxylic acids, can be transferred to the BPA storage vessel 67, if desired. However, according to an embodiment of the present invention, further processing can be performed to recycle the organic solvent by removing the BPA, as depicted in FIG. 3.

Figure 3:
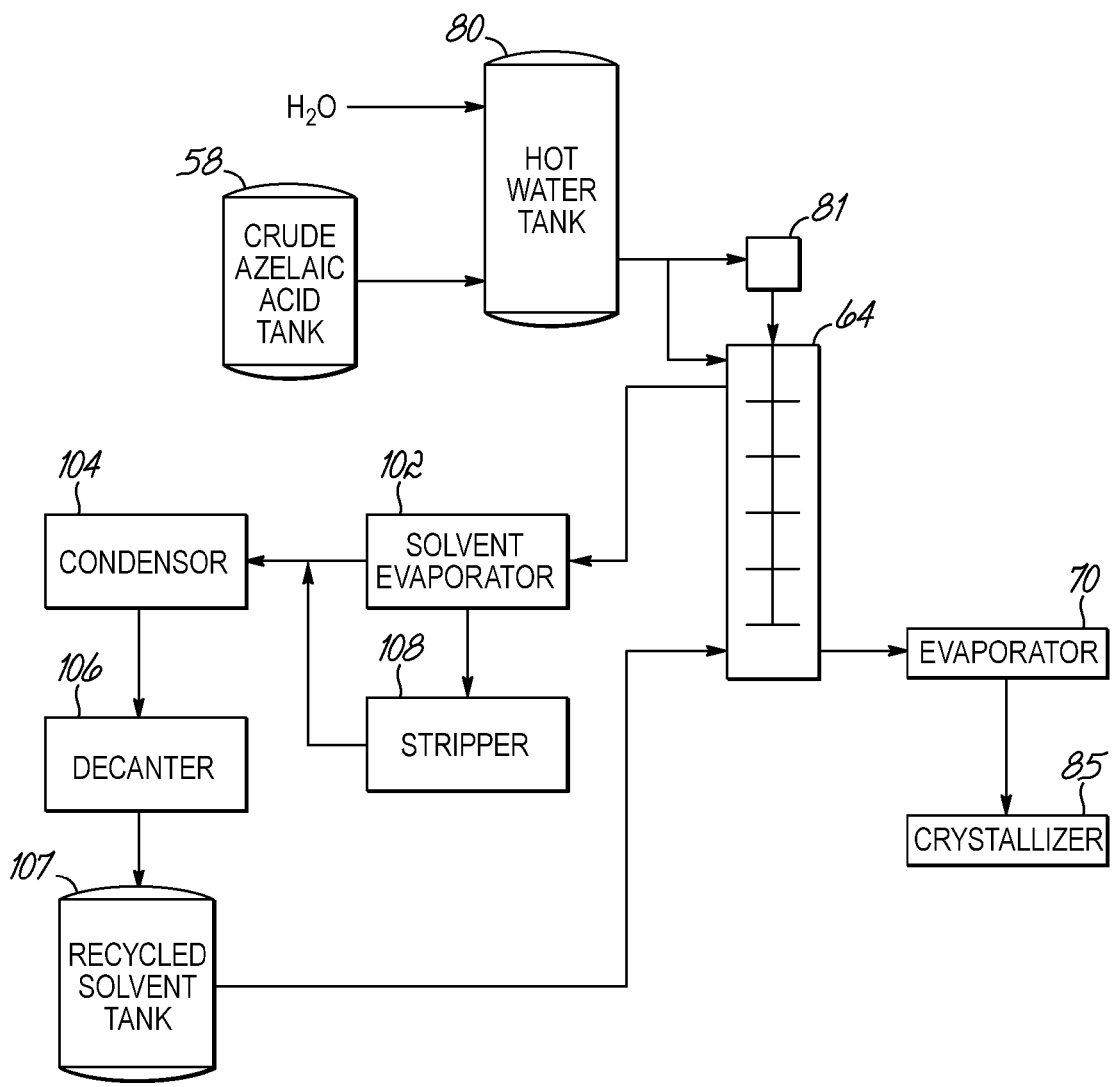
FIG. 3 is a schematic representation of an extraction purification process for azelaic acid according to an embodiment of the invention.

Referring to FIG. 3, the organic solvent layer comprising the C9 to C22 monocarboxylic acids may be transferred to an organic solvent evaporator 102, wherein the organic solvent is separated from the C9 to C22 monocarboxylic acids by vaporizing the organic solvent to form an organic solvent vapor, thereby leaving the C9 to C22 monocarboxylic acids as a residue. Any suitable conditions may be used for the organic solvent distillation unit. For example, an organic solvent evaporator may be run at about 250° F., 121° C. to about 275° F., 135° C. and atmospheric pressure. The residue containing the C9 to C22 monocarboxylic acids may be stored for later processing, if desired.

The organic solvent vapor, having been separated from the C9 to C22 monocarboxylic acids, is transported to a condenser 104, which condenses the organic solvent vapor to form the recycled organic solvent, which is then passed through a decanter 106 to remove entrained water, and may be collected in a recycled organic solvent tank 108. According to an embodiment of the invention, the recycled organic solvent includes less than 1 percent by weight of C9 to C22 monocarboxylic acids. For example, a residual content of C9 to C22 monocarboxylic acids in the recycled organic solvent may be less than 0.5 percent by weight, or less than 0.1 percent by weight, or less than 0.05 percent by weight.

The C9 to C22 monocarboxylic acids residue may be further processed by using an additional distillation unit to strip off any remaining organic solvent prior to discharging the residue. For example, the C9 to C22 monocarboxylic acids residue from the evaporator 102 may be sent to organic solvent stripper 108. The organic solvent stripper 108 uses a carrier vapor, such as steam, to strip out any remaining solvent. Any suitable conditions may be used for the organic solvent stripper 108. For example, stripper 108 may be run at approximately about 250° F., 121° C. to about 275° F., 135° C. and atmospheric pressure. The recovered organic solvent may be combined with the first distilled organic solvent prior to the condenser 104, or a standalone condenser may be used. The stripping steam is also condensed in the condenser 104, but is then separated from the solvent. For example, the water and organic solvent may be separated using the decanter 106.

The recycled organic solvent is thereby rendered sufficiently pure to then be reused to purify the azelaic acid of sufficient purity to use in preparing derivatives that may be used for a number of different purposes such as lubricants, plasticizers, lacquers, herbicides, and skin treatments.

The crystallization is facilitated by lowering the temperature of the water layer to a desired degree prior to or in the crystallizer 100. The rate of cooling may be controlled to control the crystal size and morphology. This can be achieved in a variety of crystallization techniques. In one embodiment, the temperature of the water layer may be lowered in a plurality of cooling stages. For example, the water layer may be lowered from the extracting temperature to a first temperature within a range from about 140° F., 60° C. to about 105° F., 41° C. in a first cooling stage, and from the first temperature to a second temperature within a range from about 100° F., 38° C. to about 65° F., 18° C. in a second cooling stage. In one embodiment, the first temperature is about 120° F., 50° C. and the second temperature is about 85° F., 29° C. The aqueous layer may also be seeded with seed crystals of azelaic acid at any point of the cooling process. Further, the cooling stages may be maintained for a desired duration of time. An exemplary residence time of the water layer in any cooling stage may range from about 20 minutes to about 120 minutes.

This crystallization process separates lower chain length dicarboxylic acids (e.g., C4 to C8) from the longer chain dicarboxylic acids (e.g., C9 and longer). The short chain dicarboxylic acids are retained in the mother liquor. As such, the lower chain length dicarboxylic acids, as well as any uncrystallized azelaic acid, are removed from the crystallized azelaic acid by filtration to provide a first batch of azelaic acid and the mother liquor. Portions of the uncrystallized azelaic acid retained in the mother liquor may then be recovered as explained further below.

As shown in FIG. 2, the crystallized azelaic acid from crystallizer 100 is melted in a preheater 109 to form a liquid phase, which is then transferred to a distillation unit 110, where a first distilled fraction is formed under a first set of distillation conditions (e.g., pressure, temperature). The first distilled fraction may contain residual monocarboxylic acids such as residual pelargonic acid, which are removed and transferred to a first distilled fraction storage vessel 115. The residue may be further distilled under a second set of distillation conditions to provide the final purified azelaic acid vapor, which is converted into flakes by cooling below its melting point in flaker 73 and transferred to azelaic acid storage 76.

Figure 4:
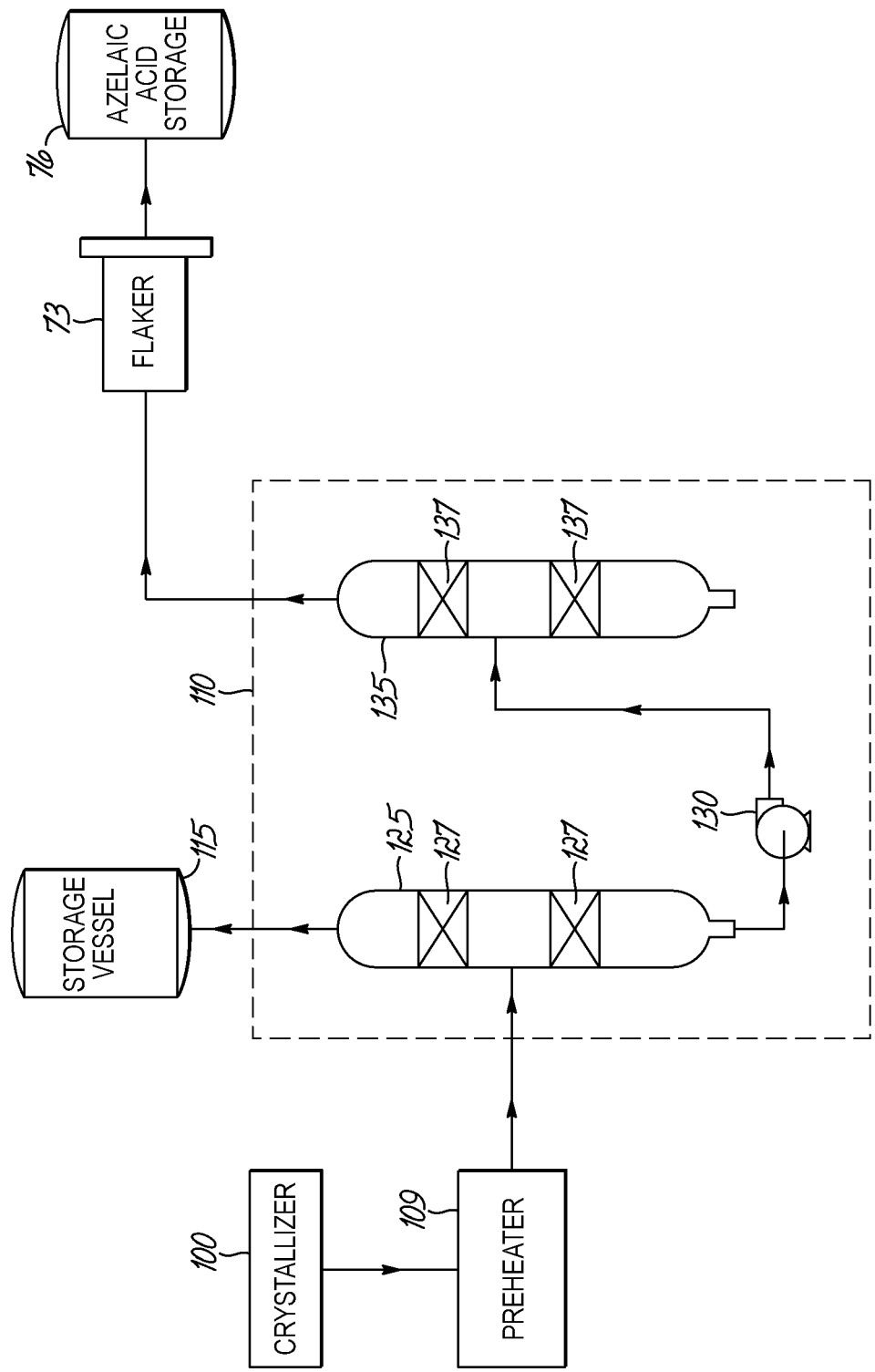
FIG. 4 is a schematic representation of a distillation purification process for azelaic acid according to an embodiment of the invention

According to an embodiment, the liquid comprising the azelaic acid can be subjected to a multi-stage distillation. As shown in FIG. 4, the first distillation can be a simple fractional distillation, which can be accomplished with a falling film still or evaporator 125 that may be configured with one or more low-pressure-loss mass transfer packings 127. In this distillation, a first distilled fraction, which may contain residual monocarboxylic acids such as residual pelargonic acid, is removed and transferred to the first distilled fraction storage vessel 115. The first residue from the first distillation can be transferred via pump 130 and subjected to a second distillation to provide a purified azelaic acid vapor. The second distillation may be performed using a thin film still or evaporator 135, such as a falling film still, a wipe film still, or a rolled film still, for example that may also be configured with one or more low-pressure-loss mass transfer packings 137. The distillate from the thin film still 135 is passed to a flaker 73, where the temperature is reduced to below the melting point, and then solid flakes of azelaic acid are conveyed to an azelaic acid storage bin 76.

For example, the solids obtained from the crystallizer 100 can be dried and then melted in a preheater 109 and then transferred to the falling film still 125, which can be operated at a low head pressure, e.g., about 1 mm Hg to about 10 mm Hg, and at a temperature in the range from about 350° F., 177° C. to about 450° F., 232° C. The residue from the fractional distillation of the liquid comprising the azelaic acid is then transferred to the thin film still 135, which can be operated at a low head pressure, e.g., about 0.5 mm Hg to about 5 mm Hg, and at a temperature in the range from about 375° F., 190° C. to about 450° F., 232° C.

The mother liquor from the multi-stage crystallization described above can be further processed to recover a significant portion of the uncrystallized azelaic acid. In one embodiment, at least a portion of the water is removed from the mother liquor to form a concentrated mother liquor and the uncrystallized azelaic acid is isolated therefrom to provide a second batch of the azelaic acid. For example, the mother liquor acids may be dried in evaporators 140. In one embodiment, the uncrystallized azelaic acid can be isolated by distilling the concentrated mother liquor to provide the second batch of azelaic acid. For example, the dried mother liquor can be fractionated in a mother liquor still 145 under appropriate distillation conditions, such as at a vacuum of about 1 mm Hg to about 10 mm Hg absolute, and at temperatures of about 400° F. to about 450° F., to recover the long chain (e.g., ≥C9) dicarboxylic acids, such as azelaic acid. The second batch of azelaic acid can be stored in an azelaic acid storage bin II 146.

In another embodiment shown in FIG. 2, the uncrystallized dicarboxylic acid can be directly obtained from the dried mother liquor to provide the second batch of the dicarboxylic acid. For example, the dried mother liquor can be transferred to a flaker 148, where the temperature is reduced to below the melting point, and then solid flakes of the dicarboxylic acid are conveyed to the azelaic acid storage bin II 146, to recover the long chain (e.g., ≥C9) dicarboxylic acids, such as azelaic acid In yet another embodiment shown in FIG. 2, the concentrated mother liquor can be transferred from the mother liquor concentrator 140 to a mother liquor crystallizer 150, wherein at least a portion of the uncrystallized dicarboxylic acid can be isolated from the concentrated mother liquor by a single stage or multi-stage crystallization to provide the second batch of the dicarboxylic acid, which can be transferred to the azelaic acid storage bin II 146. The resulting second mother liquor can be transferred to aqueous storage 160. Accordingly, a substantial increase in overall yield of the purified dicarboxylic acid may be realized.

In view of the foregoing, a higher quality purified dicarboxylic acid product, which is derived from the ozonolysis of ethylenically unsaturated C4 to C24 compounds is provided by the combination of the crystallization and distillation processes described herein. For example, the processes described herein provide, a purified dicarboxylic acid product having less than 3 wt % of a monocarboxylic acid, wherein the wt % is based on the total weight of the purified dicarboxylic acid. In another embodiment, the processes described herein provide, a purified dicarboxylic acid product having less than 1 wt % of a monocarboxylic acid, wherein the wt % is based on the total weight of the purified dicarboxylic acid. In another embodiment, the processes described herein provide, a purified dicarboxylic acid product having less than 0.5 wt % of a monocarboxylic acid, wherein the wt % is based on the total weight of the purified dicarboxylic acid. In yet another embodiment, the processes described herein provide, a purified dicarboxylic acid product having less than 0.05 wt % of a monocarboxylic acid, wherein the wt % is based on the total weight of the purified dicarboxylic acid.

The apparatus and processes described herein may be useful in the purification of dicarboxylic acids derived from ethylenically unsaturated monocarboxylic acids, such as oleic acid. As mentioned above, the apparatus and processes are particularly suited for use with an ozonolysis system that breaks down oleic acid into pelargonic acid and azelaic acid. However, the apparatus and processes may be useful to purify other dicarboxylic acids which can be derived from ethylenically unsaturated monocarboxylic acids other than oleic acid via the described ozonolysis reaction. The unsaturated acids may generally have 6 and 30 carbon atoms, for example between 8 and 24 carbon atoms, and one or more unsaturated carbon to carbon bonds. The monobasic and dibasic acid products that result from the ozonolysis reaction are determined by the location of the one or more unsaturated carbon to carbon bonds in the unsaturated acid. The unsaturated acids may be isolated from come from biological sources, such as plants, animals, or microorganisms. Alternatively, the unsaturated acids may be isolated from petroleum sources and synthetic sources. Exemplary unsaturated acids and their respective potential oxidation products are included in the Table below.

TABLE 1

Exemplary ethylenically unsaturated compounds and corresponding ozonization products.

| Carbons | Exemplary Unsaturated Fatty Acid | Exemplary Monobasic Product | Exemplary Dibasic Product |
| --- | --- | --- | --- |
| 10 | Obtusilic acid | Caproic acid | Succinic acid |
| 10 | Caproleic acid | Formic acid | Azaleic acid |
| 11 | Undecenoic acid | Formic acid | Sebacic acid |
| 12 | Lauric acid | Propionic acid | Azelaic acid |
| 14 | Myristoleic acid | Valeric acid | Azelaic acid |
| 16 | Palmitoleic acid | Heptanoic acid | Azelaic acid |
| 18 | Petroselinic acid | Lauric acid | Adipic acid |
| 18 | Oleic acid | Pelargonic acid | Azelaic acid |
| 18 | Vaccenic acid | Heptanoic acid | Hendecanedioic acid |
| 18 | Octadecenoic acid | Caproic acid | Dodecanedioic acid |
| 20 | Gadoleic acid | Undecanoic acid | Azelaic acid |
| 22 | Cetoleic acid | Undecanoic acid | Hendecanedioic acid |
| 22 | Erucic acid | Pelargonic acid | Brassylic acid |
| 24 | Selacholeic acid | Pelargonic acid | Pentadecanedioic acid |
| 26 | Hexacosenoic acid | Pelargonic acid | Heptadecanedioic acid |
| 30 | Tricosenoic acid | Pelargonic acid | Heneicosanedioic acid |

While the table above includes mono-unsaturated acids, it is understood that poly-unsaturated acids could be utilized as well. The resulting monobasic acids and dibasic acids, and their derivatives, may be used for a number of different purposes such as lubricants, plasticizers, lacquers, herbicides, and skin treatments.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and/or method and examples shown and described. The various features of exemplary embodiments described herein may be used in any combination. Accordingly, departures may be made from such details without departing from the scope of the general inventive concept.

What is claimed is:

1. A process for purifying a dicarboxylic acid comprising:
   a) ozonizing a mixture comprising an ethylenically unsaturated compound having between 6 to 24 carbons with an ozone-containing gas to form a plurality of ozonization products;
   b) cleaving the plurality of ozonization products under oxidative conditions in the presence of a suitable catalyst to form mixed oxidation products, wherein the mixed oxidation products comprise a mixture of C2 to C22 monocarboxylic acids and C2 to C22 dicarboxylic acids that includes the dicarboxylic acid;
   c) distilling the mixed oxidation products to provide a first distillate comprising a portion of the C2 to C22 monocarboxylic acids, and a first residue of the mixed oxidation products, wherein the first residue of the mixed oxidation products comprises the dicarboxylic acid and a plurality of impurity acids;
   d) distilling the first residue of the mixed oxidation products to provide a second distillate and a second residue of the mixed oxidation products, wherein the second distillate comprises the dicarboxylic acid and a first fraction of the plurality of impurity acids;
   (e) partitioning the second distillate between water and an organic solvent, wherein the water is at a temperature within the range of about 175° F., 79° C. to about 230° F., 110° C.; wherein water and the organic solvent are substantially immiscible to thereby form an aqueous layer containing the dicarboxylic acid and an organic solvent layer containing a second fraction of the plurality of impurity acids;
   f) separating the organic solvent layer from the aqueous layer;
   g) lowering the temperature of the aqueous layer to crystallize at least a portion of the dicarboxylic acid from the aqueous layer to provide a crystallized dicarboxylic acid solid and a mother liquor containing uncrystallized dicarboxylic acid and a major portion of a third fraction of the plurality of impurity acids;
   h) separating the crystallized dicarboxylic acid solid from the mother liquor to provide a first batch of the dicarboxylic acid comprising the crystallized dicarboxylic acid solid;
   i) melting the first batch of the dicarboxylic acid to form a liquid comprising the dicarboxylic acid; and
   j) distilling the liquid comprising the dicarboxylic acid to provide a purified dicarboxylic acid.

2. The process of claim 1, wherein lowering the temperature of the aqueous layer comprises cooling the aqueous layer in a plurality of cooling stages.

3. The process of claim 1, wherein lowering the temperature of the aqueous layer comprises a first cooling stage temperature within a range from about 140° F., 60° C. to about 105° F., 41° C., and a second stage cooling temperature within a range from about 100° F., 38° C. to about 65° F., 18° C.

4. The process of claim 2, wherein a residence time of the aqueous layer in any cooling stage is about 20 minutes to about 120 minutes.

5. The process of claim 1, wherein distilling the liquid comprising the dicarboxylic acid comprises a first distilling stage and a second distilling stage, wherein the first distilling stage includes distilling the liquid comprising the dicarboxylic acid to remove a first distillate fraction to provide a first residue of the liquid, and the second distilling stage includes distilling the first residue of the liquid to provide the purified dicarboxylic acid.

6. The process of claim 1, further comprising:
   k) evaporating at least a portion of the water from the mother liquor to form a concentrated mother liquor; and
   l) isolating the uncrystallized dicarboxylic acid from the concentrated mother liquor to provide a second batch of the dicarboxylic acid.

7. The process of claim 6, wherein isolating the uncrystallized dicarboxylic acid comprises distilling the concentrated mother liquor to provide the second batch of the dicarboxylic acid.

8. The process of claim 6, wherein isolating the uncrystallized dicarboxylic acid comprises crystallizing at least a portion of the uncrystallized dicarboxylic acid from the concentrated mother liquor to provide the second batch of the dicarboxylic acid.

9. The process of claim 6, wherein isolating the uncrystallized dicarboxylic acid comprises decreasing a temperature of the concentrated mother liquor below a melting point of uncrystallized dicarboxylic acid to provide a solidified product and flaking the solidified product.

10. The process of claim 6, further comprising:
    m) combining at least a portion of the first and second batches of the dicarboxylic acid prior to distilling the liquid comprising the dicarboxylic acid.

11. The process of claim 1, wherein the purified dicarboxylic acid comprises less than 3 wt % of a monocarboxylic acid, wherein the wt % is based on the total weight of the purified dicarboxylic acid.

12. The process of claim 1, wherein the purified dicarboxylic acid comprises less than 0.05 wt % of a monocarboxylic acid, wherein the wt % is based on the total weight of the purified dicarboxylic acid.

13. The process of claim 1, wherein the organic solvent is a recycled organic solvent provided by a method comprising distilling the organic solvent layer containing the mixture of C9 to C22 monocarboxylic acids to provide a recycled organic solvent, wherein the recycled organic solvent has a content of C9 to C22 monocarboxylic acids in an amount that is less than 1 percent by weight.

14. The process of claim 13, wherein the content of C9 to C22 monocarboxylic acids in the recycled organic solvent is less than 0.1 percent by weight.

15. The process of the claim 13, wherein the content of C9 to C22 monocarboxylic acids in the recycled organic solvent is less than 0.05 percent by weight.

16. The process of claim 1, wherein the aqueous layer contains less than 1 percent by weight of the organic solvent prior to any subsequent processing step.

17. The process of claim 13, wherein distilling the organic solvent layer comprises:
    1) transferring the organic solvent layer comprising the organic solvent and the mixture of C9 to C22 monocarboxylic acids to a first distillation unit, wherein the organic solvent and the mixture of C9 to C22 monocarboxylic acids are separated by forming an organic solvent vapor; and
    2) condensing the organic solvent vapor to form the recycled organic solvent.

18. The process according to claim 17, wherein the organic solvent vapor further comprises water, which is subsequently removed from the recycled organic solvent.

* * * * *